United States Patent
Kim

(10) Patent No.: US 11,207,183 B2
(45) Date of Patent: Dec. 28, 2021

(54) RVOT WIRE CAPTURING (RWC) SYSTEM IN MITRAL VALVE CERCLAGE ANNULOPLASTY

(71) Applicant: June-Hong Kim, Busan (KR)

(72) Inventor: June-Hong Kim, Busan (KR)

(73) Assignee: TAU PNU MEDICAL CO., LTD., Busan (KR)

( * ) Notice: Subject to any disclaimer, the term of this patent is extended or adjusted under 35 U.S.C. 154(b) by 0 days.

(21) Appl. No.: 14/915,443

(22) PCT Filed: Aug. 29, 2014

(86) PCT No.: PCT/IB2014/064156
§ 371 (c)(1),
(2) Date: Feb. 29, 2016

(87) PCT Pub. No.: WO2015/028986
PCT Pub. Date: Mar. 5, 2015

(65) Prior Publication Data
US 2016/0213472 A1 Jul. 28, 2016

Related U.S. Application Data

(60) Provisional application No. 61/871,353, filed on Aug. 29, 2013.

(30) Foreign Application Priority Data

Apr. 30, 2014 (KR) .......... 10-2014-0052674
Jul. 22, 2014 (KR) .......... 10-2014-0092817

(51) Int. Cl.
*A61M 25/00* (2006.01)
*A61F 2/24* (2006.01)
*A61M 25/10* (2013.01)

(52) U.S. Cl.
CPC .......... *A61F 2/2466* (2013.01); *A61F 2/2451* (2013.01); *A61M 25/10* (2013.01);
(Continued)

(58) Field of Classification Search
CPC .................. A61F 2/2451; A61F 2/2466; A61F 2230/0034; A61F 2210/009; A61M 25/10
See application file for complete search history.

(56) References Cited

U.S. PATENT DOCUMENTS 5,364,404 A * 11/1994 Jaffe ...................... A61B 17/52
606/106
5,383,852 A * 1/1995 Stevens-Wright .........................
A61M 25/0136
604/95.04

(Continued)

FOREIGN PATENT DOCUMENTS

| EP | 3158975 A1 | 4/2017 |
| WO | 2013131925 A1 | 9/2013 |

OTHER PUBLICATIONS

International Search Report of PCT/IB2014/064156, dated Dec. 3, 2014.
(Continued)

*Primary Examiner* — Dinah Baria

(57) ABSTRACT

A mitral cerclage annuloplasty apparatus includes a catheter with a blocking member and a capturing member. The blocking member is in the shape of a pigtail or a balloon, and is configured on the distal portion of the catheter preventing the catheter from traversing through an unsafe zone thereby enabling the catheter to pass through the safe zone. This prevents damage to critical cardiac tissues. The capturing member is adapted for pulling out a RVOT cerclage wire into the IVC, and comprises of an expandable and collapsible mesh so that the RVOT cerclage wire is captured and directed into the IVC through the safe zone. Thus the RVOT (Continued)

cerclage wire is passed through the RV without damaging the heart tissue forming a complete circle around the mitral valvular annulus.

5 Claims, 15 Drawing Sheets

(52) U.S. Cl.
CPC . *A61F 2210/009* (2013.01); *A61F 2230/0034* (2013.01); *A61F 2250/0003* (2013.01); *A61M 2025/1079* (2013.01)

(56) References Cited

U.S. PATENT DOCUMENTS

| | | | |
|---|---|---|---|
| 6,361,545 B1* | 3/2002 | Macoviak | A61B 17/12109 606/151 |
| 6,530,940 B2 | 3/2003 | Fisher | |
| 2002/0013571 A1 | 1/2002 | Goldfarb et al. | |
| 2004/0003819 A1 | 1/2004 | Goar et al. | |
| 2006/0195134 A1 | 8/2006 | Crittenden | |
| 2008/0200898 A1 | 8/2008 | Lashinski | |
| 2010/0030256 A1* | 2/2010 | Dubrul | A61B 10/0266 606/200 |
| 2012/0078078 A1* | 3/2012 | MacAdam | A61B 5/0422 600/381 |
| 2012/0232574 A1 | 9/2012 | Kim et al. | |
| 2013/0060328 A1 | 3/2013 | Rothstein | |
| 2013/0211510 A1 | 8/2013 | Lederman et al. | |
| 2015/0100117 A1* | 4/2015 | Bortlein | A61B 17/00234 623/2.11 |

OTHER PUBLICATIONS

Written Opinion of the International Searching Authroity, date of completion of this opinion Dec. 3, 2014.
EPO extended search report dated May 16, 2017.

* cited by examiner

RVOT WIRE CAPTURING (RWC) SYSTEM IN MITRAL VALVE CERCLAGE ANNULOPLASTY

CROSS-REFERENCE TO RELATED APPLICATIONS

This application is a 371 of PCT/162014/064156 filed Aug. 29, 2014, which claims the benefit of U.S. Provisional Application No. 61/871,353 filed on Aug. 29, 2013; Korean Patent Application No. 10-2014-0052674 filed on Apr. 30, 2014; and Korean Patent Application No. 10-2014-0092817 filed on Jul. 22, 2014, which are incorporated herein by reference in its entirety.

FIELD OF INVENTION

The present invention generally relates to techniques and devices for cardiovascular valve repair, particularly annuloplasty techniques and devices in which tensioning elements are positioned to treat regurgitation of the mitral valve in which mitral valve cerclage wire is captured and passed through the "safe zone" within the heart without damaging critical cardiac structures.

BACKGROUND

The heart is at the center of human circulatory system that pumps blood through our body unidirectionally. In order for the heart to effectively keep this unidirectional flow of blood, it must have properly functioning valves that prevent back flow through its system, or regurgitation. The heart is divided into four chambers, right and left atria, and right and left ventricles. The mitral valve (MV) separates the left atrium from the left ventricle while the tricuspid valve (TV) separates the right atrium (RA) from the right ventricle (RV).

Generally, valves should open and close completely with every heartbeat or contraction. Incomplete opening and closing of the valves cause improper flow of blood. Valvular diseases are divided into two categories, regurgitation and stenosis. Regurgitation is a failure of valve to close completely and stenosis is a failure of valve to open completely.

Mitral regurgitation (MR) is a common cardiac valve disorder where leakage of blood flow occurs due to an incomplete closure of the MV. Over time, MR burdens the heart and worsens its ability to pump blood properly eventually leading to a heart failure.

Traditional treatment of a worsening MR requires an open heart surgery with thoracotomy, cardiac arrest and cardiopulmonary bypass. Once the chest is open and access to the heart is gained, the MV is either repaired or replaced using an artificial or porcine valve.

Although very effective, this open-heart procedure is a high-risk surgery accompanied by substantial morbidity, mortality and prolonged recovery. The mortality due to the surgery itself can be as high as 5%. Hence, the procedure is reserved only for those with severe symptomatic MR and often not offered to patients who are too weak or vulnerable or have significant co-morbidity.

This high morbidity and mortality rates of an open-heart surgery have motivated further research to develop safer and less risky alternatives. Much of the research involves percutaneous approaches with the use of cardiac catheterization. Recently, this inventor filed a PCT International Application number PCT/US2007/023836 and PCT International publication number WO2008/060553 on a percutaneous approach to repairing a MR, "The MV cerclage coronary sinus annuloplasty (MVA)," which are incorporated herein in its entirety.

Briefly explained, a catheter is placed at the coronary sinus after accessing the RV 250, 350 through the jugular vein, and then a cerclage wire 120 is passed through the proximal septal vein and then through the right ventricular outflow tract ("RVOT") 152. Then the cerclage wire 120 is pulled into the RV 250, 350 thus placing the cerclage wire 120 circumferentially around the mitral annulus. Once the cerclage wire 120 is positioned, tension is applied tightening the MV and bringing together the two leaflets of the MV.

Further, in the published U.S. Patent Application Nos. 2005/0216039 and 2010/0049314, tensioning material is introduced around the MV annulus using a secondary catheter, such as a steerable guide wire or canalization catheter. The MV annulus is accessed by a number of different percutaneous approaches, including access from and through the coronary sinus. Cerclage wire is placed around the mitral annulus then tension is applied re-opposing the leaflets of the MV and reducing the defect.

While percutaneous cerclage annuloplasty is promising in valve repair, the procedure is technically demanding especially in proper positioning of the tension material around the valvular annulus to provide the proper plane of cerclage. Particularly, as the tensioning material traverses through the heart in its intramyocardial trajectory, there is a significant risk of tissue entrapment that limits the procedure and can result in serious adverse outcomes.

For example, in mitral cerclage annuloplasty, as the cerclage wire leaves the coronary sinus and enters the RVOT of the RV, if the cerclage wire must be grabbed and pulled through the RV then through the superior vena cava (SVC) or inferior vena cava (IVC). As the suture material enters the RVOT, if it is not grabbed right away and pulled into the RV, then it can undermine the ventricular structures such as chordae tendonae of the tricuspid valve (TV) 110, the papillary muscles, the moderator band and other valvular trabeculae resulting in tissue entrapment.

If tissue entrapment is not averted, entrapped tissues can be transected and irreversibly damaged resulting not only in failure of the procedure but also in other serious complications.

For this purpose, a special space between RV and RA can be defined as the "safe zone." The safe zone is defined as an imaginary space in which the cerclage wire can safely deliver therapeutic tension without damaging the TV or the moderator band 340. It should be an enclosed circular space bordered by (1) the TV leaflet and its subvalvular structures such as the chordae of TV 230, 330 and the papillary muscle, and (2) the moderator band 340. The remaining spaces between the RV and the RA other than the "safe zone" is defined here as the "unsafe zone." Therefore, a need exists for a procedure and a device that facilitates proper positioning of the cerclage wire while preventing entrapment of the ventricular tissues.

SUMMARY OF THE DISCLOSURE

The present invention includes methods, apparatus and devices for valve repair for minimally invasive, percutaneous cerclage annuloplasty. In particular, methods, apparatus and devices of the present invention facilitate MV cerclage annuloplasty. Specifically, as the cerclage wire traverses through the RV via the RVOT exit, methods and devices of the present invention are provided for properly guiding and capturing the cerclage wire through the "safe zone" averting entrapment of the critical cardiac structures.

For this purpose, a special space between RV and RA can be defined as the "safe zone." The safe zone is defined as an imaginary space in which the cerclage wire can safely deliver therapeutic tension without damaging the TV or the moderator band of the RV. It should be an enclosed circular space bordered by (1) the TV leaflet and its subvalvular structures such as the chordae of TV 230,330 and the papillary muscle, and (2) the moderator band. The remaining spaces between the RV and the RA other than the "safe zone" is defined here as the "unsafe zone."

In an exemplary embodiment, there is featured a method for performing a MV cerclage annuloplasty by introducing a cerclage capture device into the vasculature of a patient, traversing the capture device through the safe zone, methods of testing or ensuring that the capturing device traversed through the safe zone, positioning the capturing device at an ideal location of a cerclage trajectory, capturing the cerclage wire, and guiding the cerclage wire back through the safe zone preventing capture, entrapment or damage to critical cardiac structures.

In accordance with the present invention, the ideal cerclage trajectory comprises the coronary sinus, the basal interventricular septum, the RVOT exit, the RV and the IVC. An exemplary embodiment comprises a catheter with a blocking member and a capturing member. The blocking member is configured on the distal portion of the catheter. The blocking member prevents the catheter from traversing through an unsafe zone and enables the catheter to pass through a safe zone thereby circumventing damage to the tricuspid valvular structures and the moderator band of the right ventricle. The capturing member is configured proximal to the blocking member, wherein the capturing member is adapted for pulling out a RVOT wire through the IVC. The RVOT wire is positioned in the RV through the SVC and the CS prior to being captured by the capturing member. The blocking member is generally configured in the shape of a pigtail or in the shape of a balloon that is inflatable and deflatable using a control located outside of the patient's body. The capturing member further comprises a mesh which is collapsible and expandable using a control located outside of the patient's body. When the mesh is expanded, the RVOT wire passes through the mesh, and when the mesh is collapsed, the RVOT wire is securely grabbed by the mesh enabling the catheter to pull out the RVOT wire into the IVC. In another embodiment, the capturing member further comprises a magnet adapted for magnetically capturing the RVOT wire.

Further, the catheter comprises of a lumen adapted for passing a guide wire 400, 500, 600 through the catheter 125, 410. The surface of the capturing member can also be formed of a radio-opaque material adapted for visualizing the capturing catheter 121 to confirm its location radiographically. Yet, in another embodiment, the capturing member 121 comprises of a central lumen catheter 125, 134, an outer catheter 122 and a mesh 124. The central lumen catheter 125, 134, 410 holds the guide wire 400, 500, 600, wherein the outer catheter 122 holds the central lumen catheter 125, 134 enabling the central lumen catheter 125, 134 to move in and out. The distal portion of the mesh is gathered and secured to the central lumen catheter 125, 134 and the proximal portion of the mesh is gathered and secured to the outer catheter. Additionally, the capturing member comprises of at least one connector(s) 141, 145, 157 which attaches the mesh to the central lumen catheter 125, 134 allowing the connector(s) 141, 145, 157 to move back and forth causing the mesh to expand and collapse thereby forming a D-shape when the mesh is expanded.

In another exemplary embodiment of the present invention, there is another method for directing a RVOT wire into the IVC in cerclage annuloplasty. This method comprises of inserting a safe-zone catheter through the IVC, passing through a safe zone of the RV, preventing passage through an unsafe zone thereby circumventing damage to the tricuspid valvular structures and the moderator band 240, 340 of the RV, and positioning the distal end of the safe-zone catheter at the RV and the Pulmonary Artery (PA) 100, 310, 530, while positioning the RVOT wire in the RV through the SVC and the CS. Then a guide wire is inserted through a lumen of the safe-zone catheter, the safe-zone catheter is removed while keeping the guide wire in its place, a capturing catheter is inserted along the guide wire to the RV to capture the RVOT wire, and the RVOT wire is directed so that the capturing catheter steers the captured RVOT wire into the IVC.

The safe zone is further defined as an imaginary space in which the cerclage material can safely traverse through the right ventricle and deliver therapeutic tension without damaging the TV and the moderator band of the RV, wherein the safe zone is an enclosed circular space bordered by (1) the subvalvular structures such as the TV leaflet, chordae of TV 230,330, and the papillary muscle, and (2) the moderator band, and wherein the remaining space between the RV and the RA other than the safe zone is defined here as the unsafe zone.

In this exemplary body, a blocking member is further comprised on the distal portion of the safe-zone catheter, wherein the blocking member prevents the safe-zone catheter from traversing through the unsafe zone and enables the safe-zone catheter to pass through the safe zone thereby circumventing damage to the tricuspid valvular structures and the moderator band of the RV. The blocking member is generally configured in the shape of a pigtail, or in the shape of a balloon that is inflatable and deflatable using a control located outside of the patient's body. The capturing catheter further comprises a mesh which is collapsible and expandable also using a control located outside of the patient's body. When the mesh is expanded, the RVOT wire passes through the mesh, and when the mesh is collapsed, the RVOT wire is firmly grabbed by the mesh enabling the capturing catheter to pull out the RVOT wire through the IVC. The capturing catheter further comprises a magnet adapted for magnetically capturing the RVOT wire. Each of the safe-zone catheter and the capturing catheter further comprises a lumen adapted for passing a guide wire through.

Furthermore, the outer surface of the capturing catheter is formed of a radio-opaque material adapted for visualizing the capturing catheter to confirm its location radiographically. The capturing catheter 121 further comprises a central lumen catheter 125, 134, an outer catheter 122 and a mesh 124 wherein the central lumen catheter 125, 134 which holds a wire. The outer catheter 122 holds the central lumen catheter 125, 134 enabling the central lumen catheter 125, 134 to move back and forth within the outer catheter 122. The distal portion of the mesh 124 is gathered and secured to the central lumen catheter 125, 134, and the proximal portion of the mesh 124 is gathered and secured to the outer catheter 122. The capturing catheter further comprises at least one connector(s) 141, 145, 157 which attaches the mesh to the central lumen catheter 125, 134 allowing the connector(s) 141, 145, 157 to move back and forth along the central lumen catheter 125, 134 causing the mesh to expand and collapse thereby forming a D-shape when the mesh is expanded.

DETAILED DESCRIPTION

The present invention feature methods and devices for repairing a cardiac valve in a patient. In particular, methods and devices are for treatment of valvular regurgitation in a cerclage annuloplasty procedure. It is noted, while the methods and devices described in particular is in connection with the MV regurgitation repair, such methods and devices can also be utilized for repairs of other valves. The detailed disclosure of the RVOT Wire Capturing (RWC) system methods and devices will be disclosed.

Methods of the current invention generally include ensuring the RVOT wire, which has entered the RV through the SVC, the CS and the RVOT, safely passes through the safe zone into the IVC without damaging the TV structures and the moderator band 340.

Methods of the invention generally include the RWC catheter device comprising a safe-zone catheter, a guide wire that passes through the catheter lumen, and a RVOT wire capturing catheter will be discussed in detail. Additionally, an embodiment where the safe-zone catheter and the RVOT wire capturing catheter functioning as unibody will be discussed in detail as well.

In MV cerclage annuloplasty procedure, a wire is inserted into a tube that has passed through the SVC and the CS. Then a catheter is inserted over the wire through the SVC and the CS. At that point, a contrast media is injected into the catheter to visualize and confirm the location of catheter within the CS. Then the wire is removed and the RVOT wire is introduced through the catheter. Subsequently, the RVOT wire passes through the basal interventricular septum exiting through the RVOT into the RV, and thus, the RVOT wire is named as the RVOT cerclage wire. In another words, in MV cerclage annuloplasty, the RVOT cerclage wire is defined as a cerclage wire that passes through the ideal trajectory of the coronary sinus, the interventricular septum and the RVOT into the RV thus encircling the MV.

Figure 10:
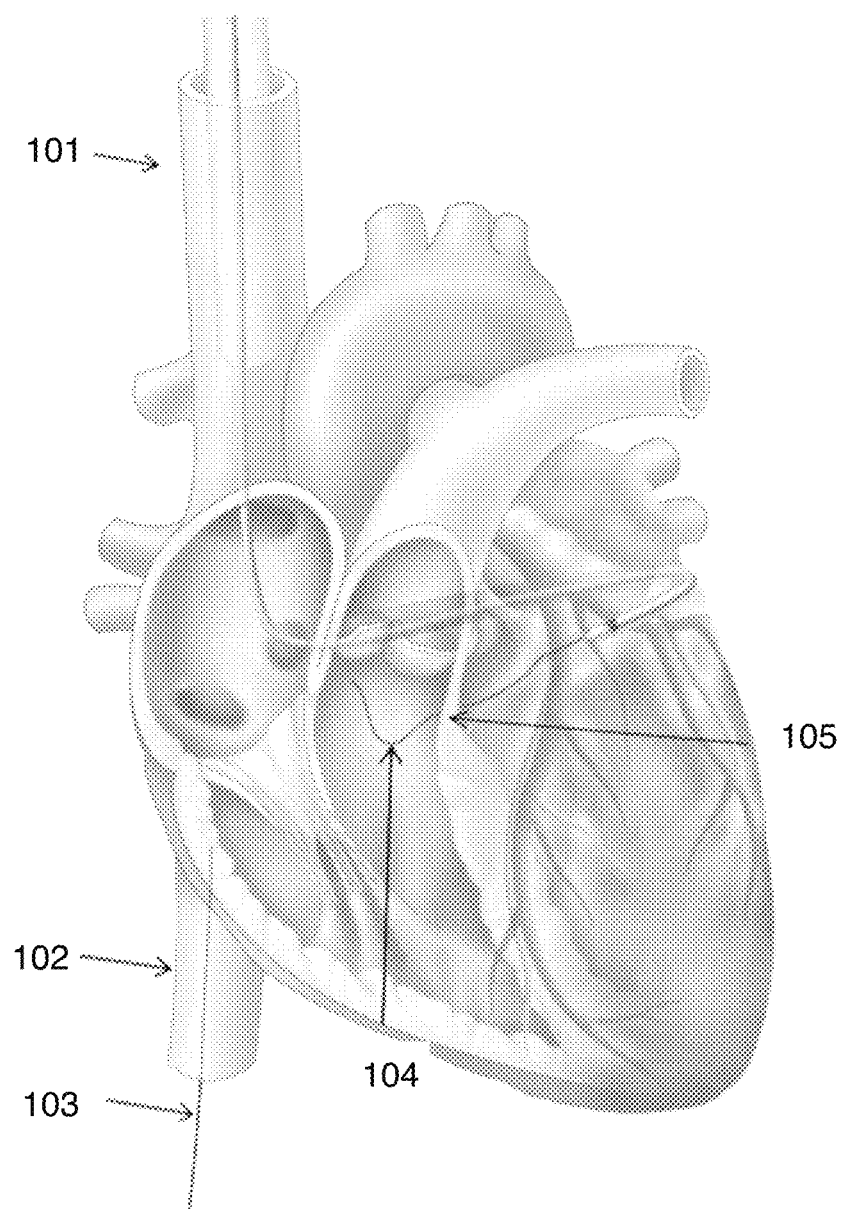
FIG. 10 is an anatomical view of the RVOT cerclage wire traversing through the SVC and the CS. Then the RVOT cerclage wire exits the CS through the RVOT into the RV.

In FIG. 10 is a schematic drawing of the heart showing the RVOT cerclage wire 104 as it traverses through the SVC 101, the CS and the RVOT 105 into the RV.

In MV cerclage annuloplasty procedure, a RVOT cerclage wire 104 traverses through the SVC 101, the CS and the RV then back through the SVC 101 thus forming a circle around the MV.

In order to steer the RVOT cerclage wire 104 back into the SVC, the current invention comprises devices and methods to direct the RVOT cerclage wire 104 first into the IVC 102.

In order to direct the RVOT cerclage wire into the IVC, first, the safe-zone catheter is inserted through the IVC into the RV passing through the safe zone. Then a guide wire is passed through the safe-zone catheter, thus ideally positioning at the PA. Then, the safe-zone catheter is removed and the RVOT cerclage wire capturing catheter is inserted over the guide wire into the RV positioning at the PA. Then RVOT cerclage wire is captured by the capturing catheter and the catheter is directed to the IVC steering the captured RVOT cerclage wire into the IVC. Then a snare is introduced through the SVC which can grab the RVOT cerclage wire from the IVC into the SVC, thus completing the circle around the MV.

The current invention includes devices and methods for traversing through the safe zone of the RV in a MV cerclage annuloplasty procedure comprising a safe-zone catheter, a guide wire that passes through the IVC into the RV, a RVOT cerclage wire capturing catheter, and methods for using the said devices for directing the ROVT wire into the IVC.

Figure 4:
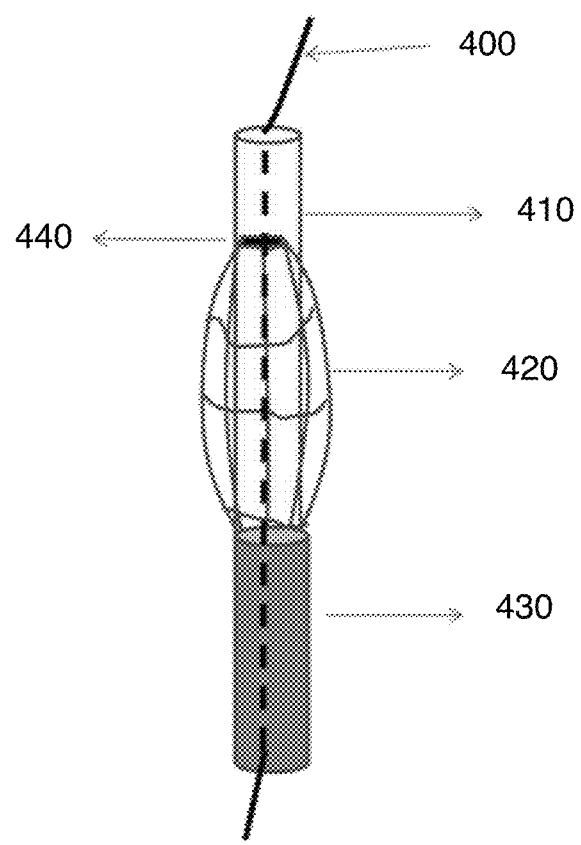
FIG. 4 is a schematic drawing of the MV cerclage annuloplasty RWC catheter device comprising the guide wire 400, the central lumen catheter 410, the mesh 420 and the outer catheter 430.
Figure 12:
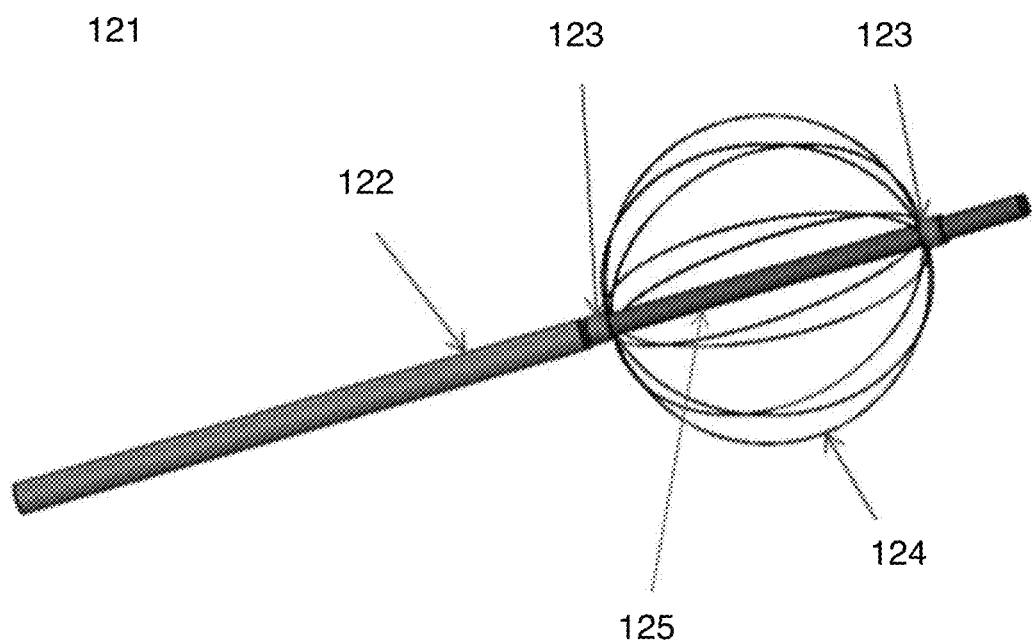
FIG. 12 shows a drawing of another embodiment of the MV cerclage annuloplasty RWC device comprising a capturing catheter with a mesh on the distal end of the catheter.

The capturing catheter as shown in FIGS. 4 and 12 refers to the catheter used to capture the RVOT cerclage wire and since the capturing catheter directs the RVOT cerclage wire into the IVC, the catheter may be called RVOT cerclage wire steering device.

In accordance with the current MV cerclage annuloplasty invention, prior to capturing the RVOT cerclage wire 540, a guide wire 500 enters into the RV and ends at the PA via the safe-zone catheter which traverses through the femoral vein, the IVC, the RV and the PA. Here, the guide wire 500 is named since the purpose of the guide wire is to guide the capturing catheter into the RV. Thus the guide wire 500 must traverse through the safe zone of the RV.

Figure 1:
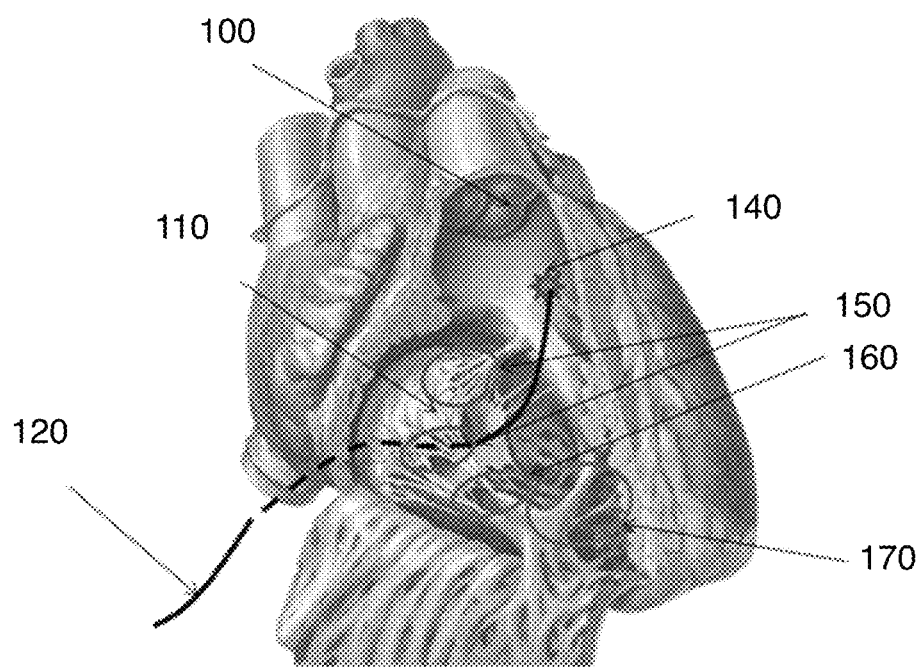
FIG. 1 shows anatomical structures and the safe trajectory for the MV cerclage annuloplasty wire exiting the RVOT into the RV and then exiting through the IVC. Also shown are the potentially vulnerable cardiac structures that can be entrapped and damaged.
Figure 2:
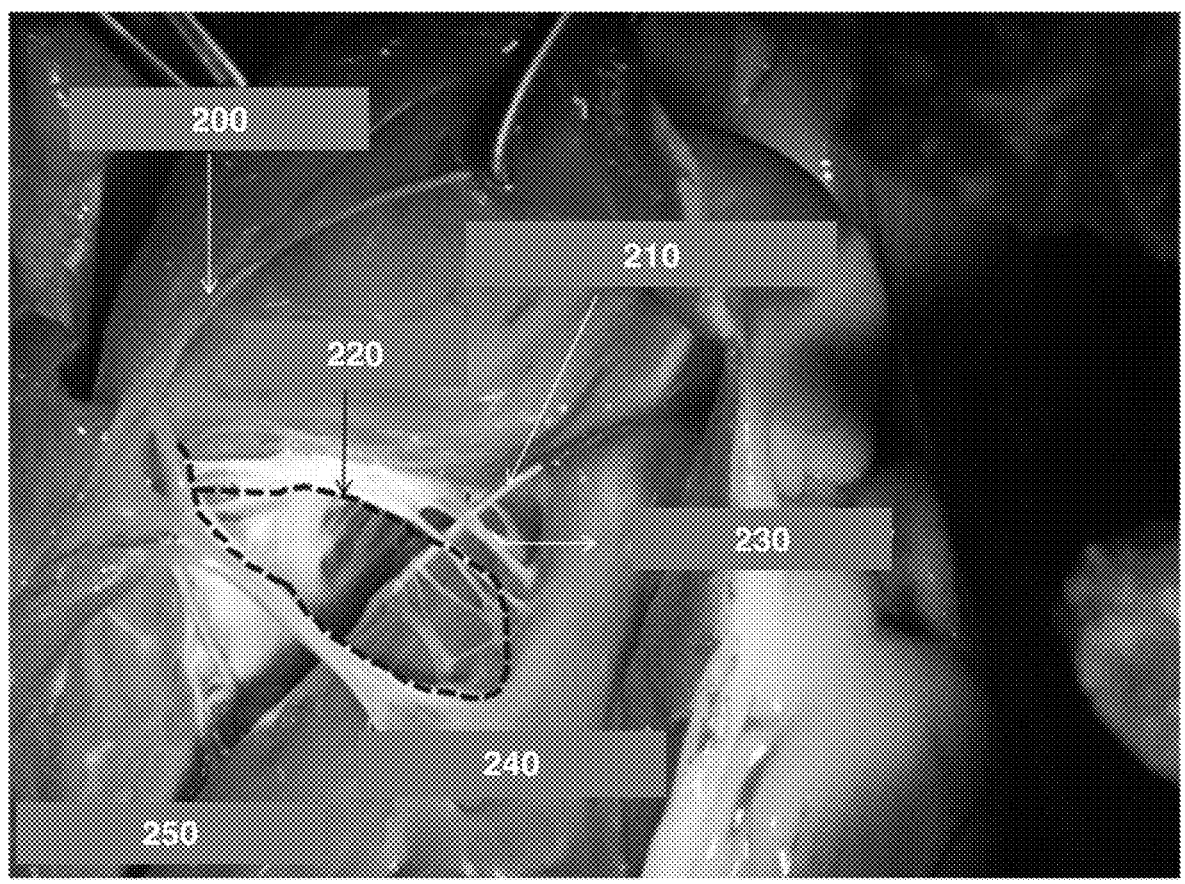
FIG. 2 shows a close up anatomical view of a wire passing through the safe zone 200, 320 and a wire passing through the unsafe zone 210, 300.
Figure 3:
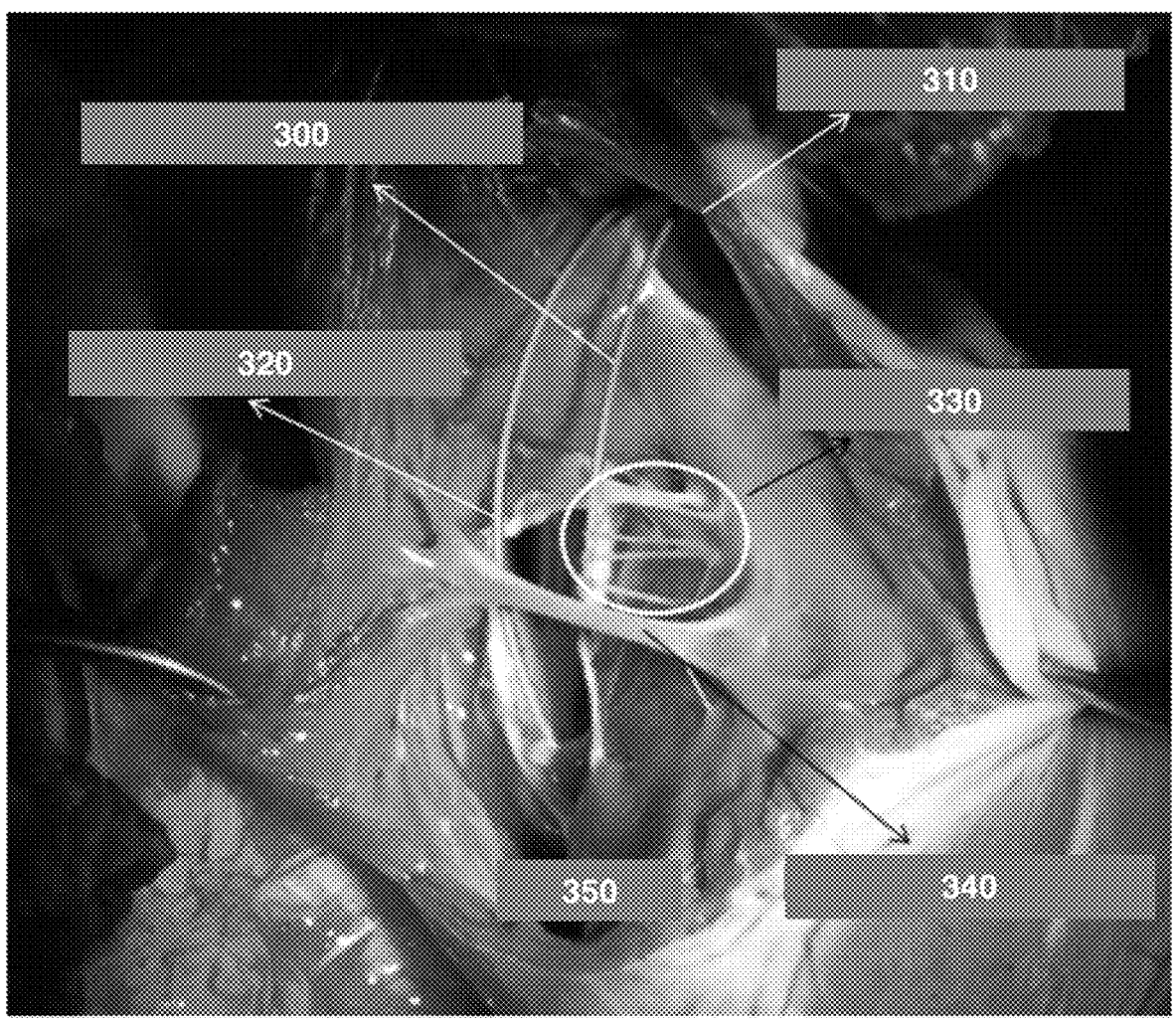
FIG. 3 shows another close up anatomical view of the wires in the safe zone and the unsafe zone.

FIG. 1 shows an anatomical structures and the safe trajectory for the MV cerclage annuloplasty wire exiting the RVOT into the RV and the unsafe trajectory where the potentially vulnerable cardiac structures that can be entrapped and damaged. FIG. 2 and FIG. 3 show an anatomical view of a wire passing through the safe zone 120 and a wire 210, 300 passing through the unsafe zone.

FIGS. 1-3 show the critical cardiac structures in the RV such as the TV leaflets, the chordae of TV 150, 230, 330, papillary muscles 160 and the moderator band 170, 340. These valvular structures and the moderator band are critical to the proper functioning of the RV, therefore, such structures should not be damaged by cerclage wire or catheters. Accordingly, in MV cerclage annuloplasty procedure the safe-zone catheter should traverse through the safe zone wherein the safe zone is an enclosed circular space bordered by (1) the subvalvular structures such as the TV leaflet, chordae of TV 230, 330, and the papillary muscle 160, and (2) the moderator band 170, 340. The remaining space between the RV and the RA other than the safe zone is defined here as the unsafe zone. Hence the unsafe zone is the space in the RV where the subvalvular structures such as the TV leaflet, chordae of TV 230, 330 and the papillary muscle, and the moderator band 170, 340 can be damaged by the cerclage wire.

FIG. 2 clearly shows the difference of the safe zone 220 and the unsafe zone. As shown in FIG. 2 and FIG. 3, if the catheter passes through the unsafe zone and tension is applied in this pathway, critical heart tissues can be seriously and irreversibly damaged. Therefore, a cerclage wire or a catheter must pass through the safe zone 220 and whether a cerclage wire or a catheter passed through the safe zone must be confirmed.

Figure 7:
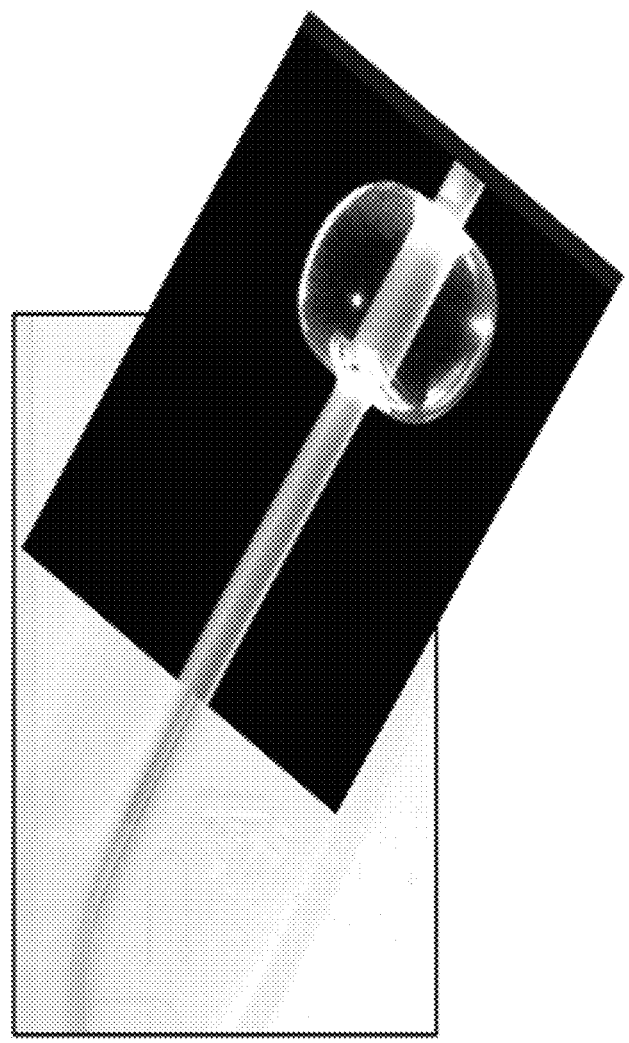
FIG. 7 is another embodiment of MV cerclage annuloplasty RWC device comprising a safe-zone catheter having a balloon-shaped blocking member. Balloon is inflated to prevent the catheter from passing through the unsafe zone. Due to the size of the inflated balloon, the catheter can only pass through the safe zone.
Figure 8:
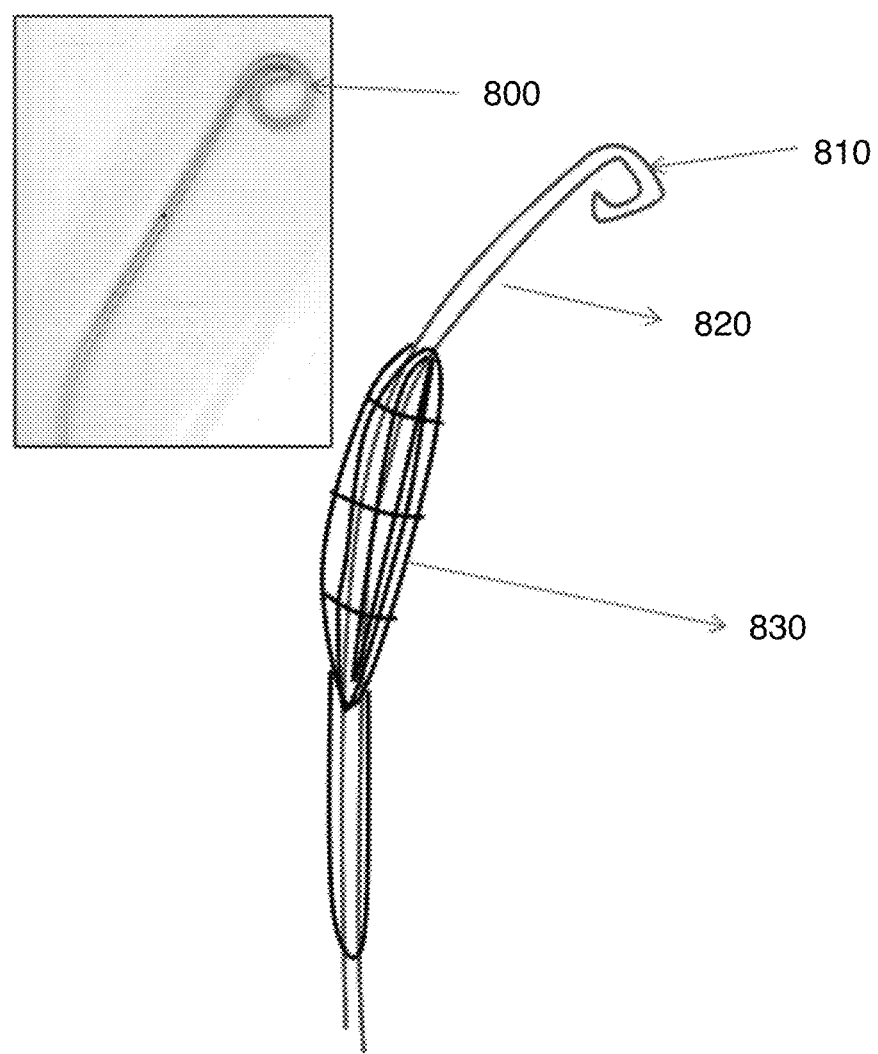
FIG. 8 is a drawing of another embodiment of MV cerclage annuloplasty RWC device comprising a safe-zone catheter having a pigtail-shaped blocking member on the distal end of the catheter and having a mesh proximal to the pigtail-shaped blocking member.
Figure 11:
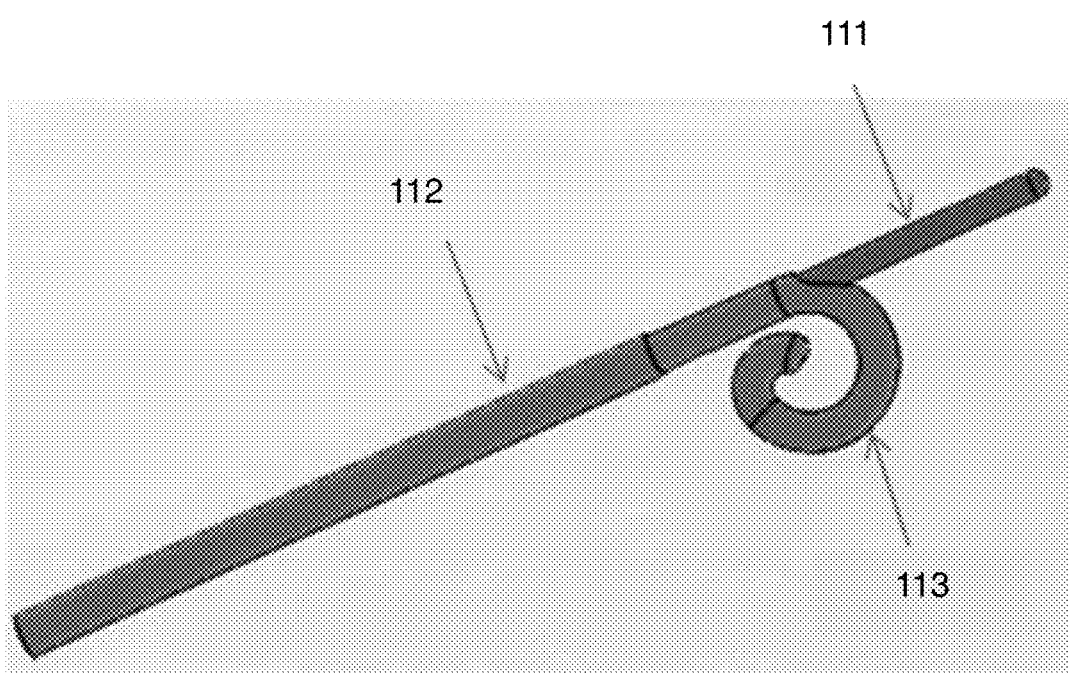
FIG. 11 shows a drawing of the MV cerclage annuloplasty RWC device comprising a safe-zone catheter having a pigtail-shaped blocking member on the distal end of the catheter, and a guide wire passing through the lumen of the catheter.

Thus, safe-zone catheter as shown FIGS. 7, 8, and 11 refers to a catheter that passes through the safe zone and can be confirmed that it indeed has traversed through the safe zone.

In the current invention, the safe-zone catheter comprises a balloon-shaped blocking member or pigtail-shaped blocking member as shown FIGS. 7, 8, and 11. Additionally, the safe-zone catheter is inserted through the IVC instead of the SVC then is directed through the RV and into PA.

FIGS. 7, 8 and 11 disclose methods for verifying whether or not the catheter or the cerclage wire passed through the safe zone, and methods for preventing the passage of the catheter or the cerclage wire through the unsafe zone.

FIG. 7 shows one embodiment of the safe-zone catheter of the current invention with a balloon-shaped blocking member, and the FIG. 8 shows another embodiment of the safe-zone catheter with a pigtail-shaped blocking member 810 and a mesh 830 located proximal to the pigtail-shaped blocking member. FIG. 11 shows the safe-zone catheter with the pigtail-shaped blocking member 113 and a guide wire 111 passing through the lumen of the safe-zone catheter.

First, according to the FIG. 7, a balloon-shaped blocking member is on the distal end of the safe-zone catheter preventing the passage of the safe-zone catheter through the unsafe zone.

The blocking member of the safe-zone catheter provides a method of freely passing through the safe zone of the TV and the RV while preventing the passage through the unsafe zone. Namely, the blocking member prevents the safe-zone catheter from passing through the unsafe zone and assists the blocking member to traverse only through the safe zone.

The safe-zone catheter with the balloon-shaped blocking member first enters through the IVC, then air is injected into the balloon using the outside control thus assisting the safe-zone catheter to traverse only through the safe zone. In other words, once the balloon enters into the unsafe zone, further advancement into the heart is prevented. Hence, when the inflated balloon no longer advances, the safe-zone catheter can be repeatedly withdrawn and re-entered until the catheter enters through the safe zone freely. Also, the reason why the safe-zone catheter is semi-rigid and the PA is approached from the IVC is to prevent the catheter from entering into a portion of the unsafe zone between the moderator band and the RV wall.

FIG. 8 shows the pigtail-shaped blocking member positioned at the distal end of the safe-zone catheter. Upper left picture 800 in FIG. 8 shows the pigtail-shaped blocking member positioned at the distal end of the safe-zone catheter, and central picture in FIG. 8 shows the pigtail-shaped blocking member 810 positioned at the distal end 820 of the safe-zone catheter and a mesh situated proximal to the pigtail-shaped blocking member. In other words, the central picture in FIG. 8 shows the combined safe-zone catheter 820 and the cerclage wired capturing catheter 830.

As shown in FIG. 8, since the catheter has a pigtail-shaped distal end 810, the catheter is able to pass through the safe zone of the RV to the PA. The enlarged size of the pigtail-shaped end acts as the blocking agent thereby assisting the safe passage of the safe-zone catheter. If pig-tail shaped safe-zone catheter enters into the unsafe zone, it can no longer advance through the heart. When the safe-zone catheter does not advance, it can be withdrawn and re-advanced repeatedly until it advances further through the safe zone into the PA.

Meanwhile, FIG. 11 shows a drawing of the MV cerclage annuloplasty RWC device comprising a safe-zone catheter having a pigtail-shaped blocking member 113 on the distal end of the catheter 112, and a guide wire 111 passing through the lumen of the safe-zone catheter. The distal end 113 of the safe-zone catheter is shaped in a pigtail-shape so that the safe-zone catheter can pass through the safe zone, and the safe-zone catheter comprises a lumen that allows the passage of a guide wire 111. Also, the reason why the safe-zone catheter is semi-rigid and the PA is approached from the IVC is to prevent the catheter from entering into a portion of the unsafe zone between the moderator band and the RV wall.

In an experiment using a 40-50 kg pig, this inventor selectively used a pigtail and a balloon that was 1 cm in diameter to pass through the safe zone. The inventor verified that Pigtail or balloon greater than 1 cm in diameter was not able to pass into the unsafe zone. Therefore, in order to pass through the safe zone, the pigtail or the balloon needs be greater than 1 cm in diameter approximately.

Figure 5:
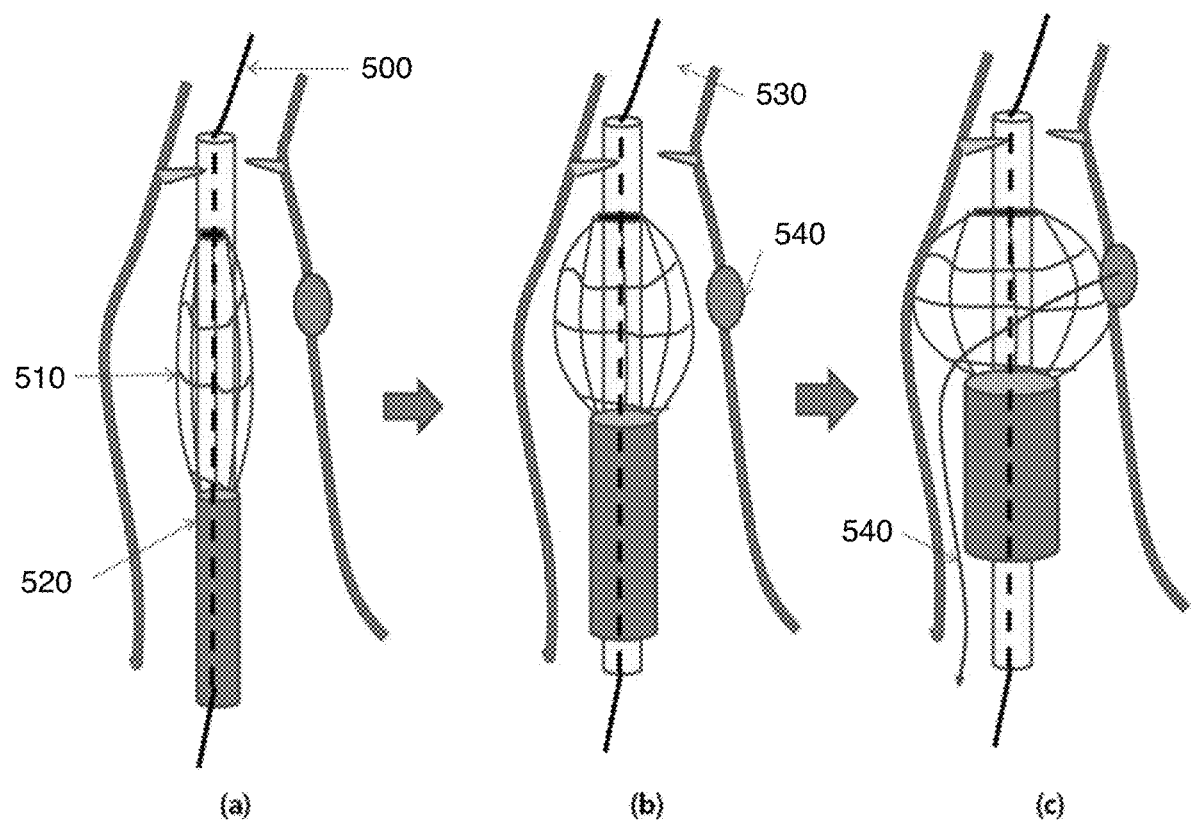
FIGS. 5 and 6 show a schematic view of the RWC catheter device in operation. First, the RWC catheter device is traversed through the safe zone and placed in the PA near the RVOT exit 140, 620. Second, the mesh is expanded. Third, the RVOT cerclage wire entering the RV through the RVOT exit passes through the mesh. Fourth, the mesh is collapsed capturing the RVOT cerclage wire. Finally, the RWC wire capturing catheter is directed into IVC bringing the captured RVOT cerclage wire with it through the safe zone.
Figure 6:
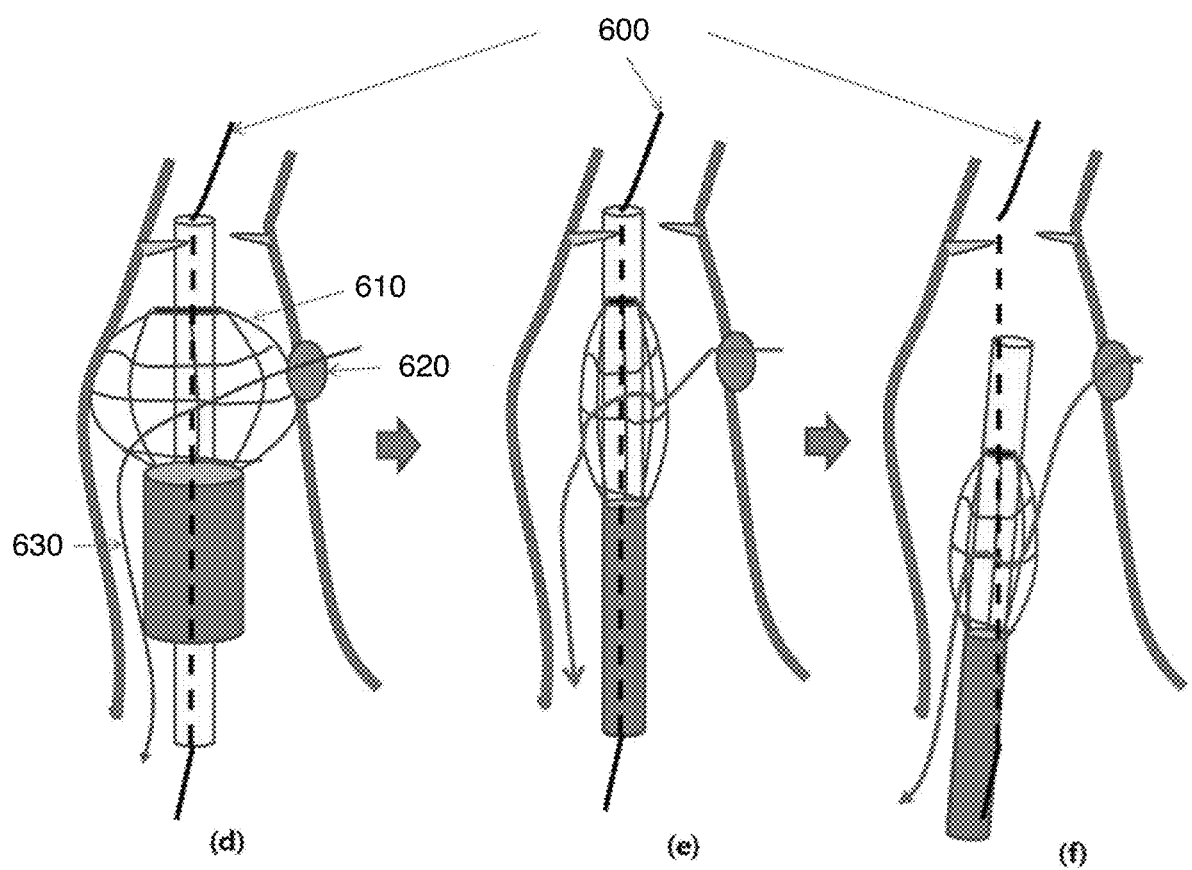

Once safe-zone catheter passes through the safe zone and is positioned in the PA, a guide wire 111, 151, 400, 500, 600 is inserted through the safe-zone catheter. Preferable, the guide wire should be passed into the PA and positioned at the entry of the PA. Then the safe-zone catheter is removed keeping the guide wire positioned at the PA. Then the capture catheter as shown in FIGS. 4 and 12 is threaded over the guide wire through the safe zone 200, 320 into the PA to capture the RVOT cerclage wire 104, 540, 630 as shown in FIGS. 5-6.

FIG. 4 is a schematic drawing of the capture catheter of the MV cerclage annuloplasty comprising the guide wire 400, the central lumen catheter 410, the mesh 420 and the outer catheter 430. In other words, the RVOT cerclage wire 540 which passed through the SVC or the IVC then through the interventricular septum exiting through RVOT 152 into the RV is captured by the capture catheter and directed from the PA into the IVC. The capture catheter is named to indicate that it functions to capture the RVOT cerclage wire 540, and thus can also be called RVOT wire capture catheter.

FIG. 4 also shows the mesh 420 of the capture catheter device. The mesh 420 remains collapsed until the capture catheter reaches the RV and is expanded once it is the RV near the PA to facilitate easy passage of the RVOT cerclage wire 540 through the mesh 420 as shown in FIG. 5. Once the RVOT cerclage wire passes through the mesh, the mesh is collapsed capturing the RVOT cerclage as shown in FIG. 6. In other words, the mesh is collapsed or expanded from a control located outside the patient's body and when it is expanded, the mesh 420, 510 is configured so that the RVOT cerclage wire 540 easily passes through the mesh, and when it is collapsed, it can firmly grab the RVOT cerclage wire.

To summarize the capture catheter, the mesh is passed through the IVC into the RV near the PA. Since the capture catheter as shown in FIG. 4 passes over the guide wire 400, 500, 600 which has already traversed through the safe zone, the capture catheter and the mesh placed on the distal portion of the capture catheter can only pass through the safe zone of the RV. Radiographic imaging can be utilized to confirm the position of the mesh and the RVOT cerclage wire. The mesh composes of radio-opaque marker 132 so that it is adapted for visualizing to confirm its location radiographically. Then the mesh 420, 510, 610 is expanded to allow easy passage of the RVOT cerclage wire 540, 630. Once the RVOT cerclage wire passes through the mesh, the mesh is collapsed as shown in FIG. 6 using the control located outside the patient's body capturing the RVOT cerclage wire 540, 630.

FIGS. 5 and 6 show how the capture catheter captures the RVOT cerclage wire 540, 630. FIG. 5(*a*) shows the capture catheter 520 positioned inside the RV, FIG. 5(*b*) shows the capture catheter with the expanded mesh, FIG. 5(*c*) and FIG. 6(*d*) show the RVOT cerclage wire 630 passing through the expanded mesh 610, FIG. 6(*e*) shows collapsed mesh with captured RVOT cerclage wire, and FIG. 6(*f*) shows the capture catheter being directed into the IVC thus steering with it the captured RVOT cerclage wire.

Though it is not shown in the Figures, instead of the mesh, the capture member of the capture catheter can be formed of a magnetic material to capture the RVOT cerclage wire magnetically. The RVOT cerclage wire or the distal end of the RVOT cerclage wire must be also formed of a magnetic material.

Figure 9A:
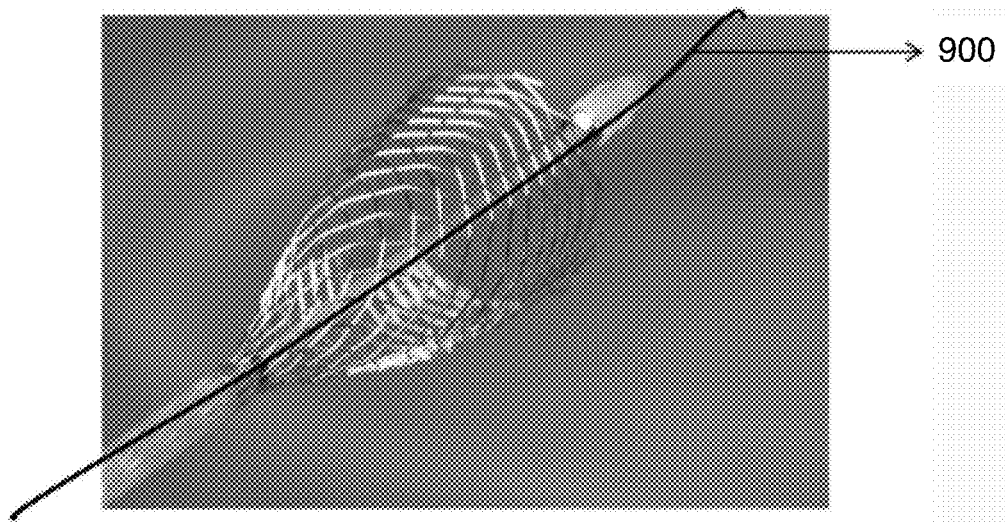
FIG. 9*a* shows a wall stent currently used as a self expanding stent in an angioplasty procedure requiring modifications to be used as the mesh in the RWC catheter device.
Figure 9B:
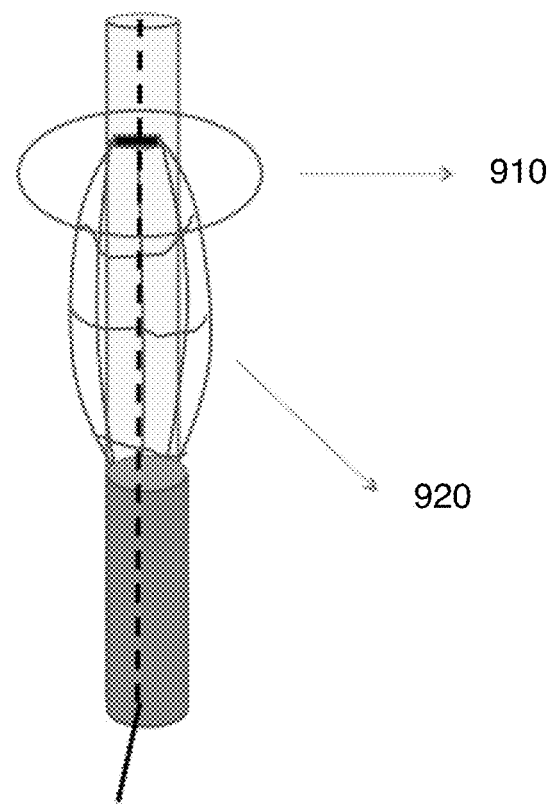
FIG. 9*b* is a schematic drawing of the self expanding mesh with closed upper part and a sheath or a catheter covering the mesh. The mesh sheath or the catheter can be used to control the expansion size of the mesh.

FIG. 9(*a*) shows a wall stent 900 currently used as a self expanding stent in an angioplasty procedure requiring modifications to be used as the mesh 920 in the RWC catheter device. FIG. 9(*b*) is a schematic drawing of the self expanding mesh with closed upper part 910 and a sheath or a catheter covering the mesh 920. The mesh sheath or the catheter can be used to control the expansion size of the mesh 920.

FIG. 12 shows a drawing of another capturing embodiment 121 of the MV cerclage annuloplasty RWC device comprising the outer catheter 122 and the central lumen catheter 125 with a mesh 124 positioned between the distal end of the outer catheter 122 and the central lumen catheter 125. Since the capture catheter 121 is inserted over the guide wire 400, 500, 600 into the RV, the capture catheter has a lumen to allow the passage of the guide wire. The proximal or the distal portion of the mesh can be formed of radio-opaque marker 123, 132 in FIGS. 12 and 13 so that it can be visualized radiographically from the outside to confirm the location of the mesh and the capture catheter.

Although, the safe-zone catheter and the capture catheter are described above separately, the two catheters can be combined into one unit 131 so that it has can have both functions and is included within the scope of this invention. This is shown and briefly described in FIG. 8 and also in FIG. 13.

Figure 13:
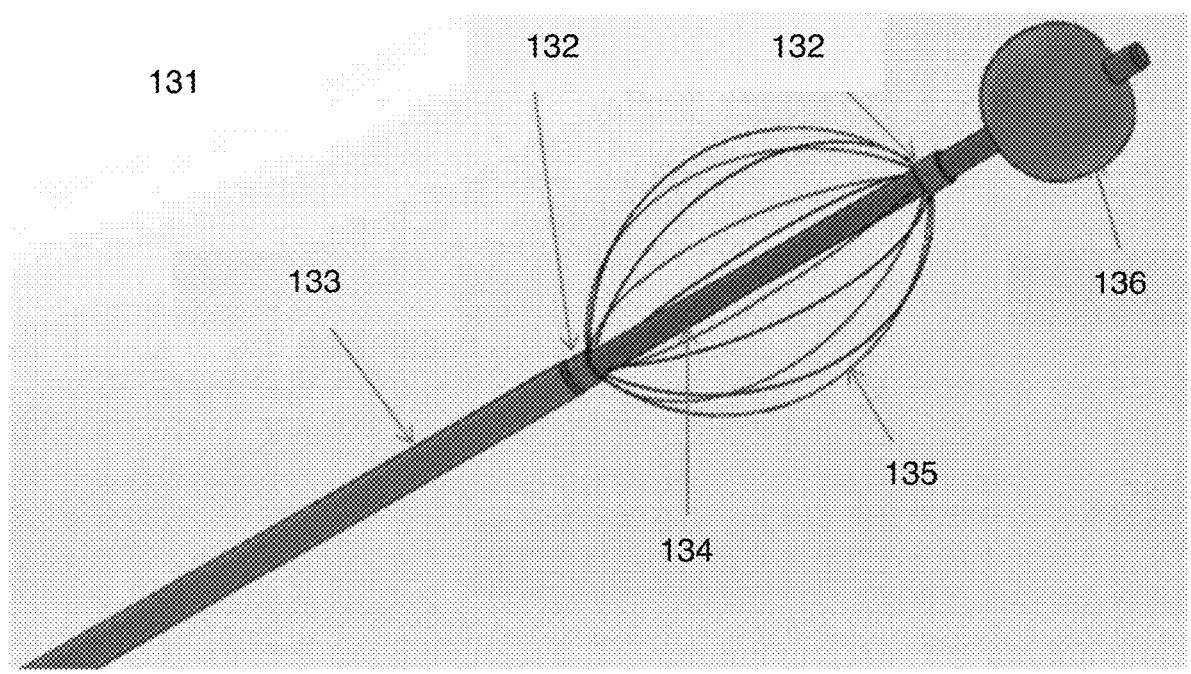
FIG. 13 shows a drawing of another embodiment of MV cerclage annuloplasty RWC device comprising a safe-zone catheter having a balloon-shaped blocking member on the distal end of the catheter, and a mesh proximal to the balloon-shaped blocking member.

FIG. 13 shows a drawing of another embodiment of MV cerclage annuloplasty RWC device 131 comprising a safe-zone catheter having a balloon-shaped blocking member 136 on the distal end of the catheter, and a mesh 135 proximal to the balloon-shaped blocking member 136. FIG. 8 and FIG. 13 both contain the safe-zone catheter's blocking member 136, 810 as well as the capture catheter's capturing member in one body.

RVOT cerclage wire is captured by the capturing catheter and the catheter is directed to the IVC steering the captured RVOT cerclage wire into the IVC. Then a snare is introduced through the SVC to grab the RVOT cerclage wire from the IVC into the SVC, thus completing the circle around the MV annulus.

As described above, during the MV cerclage annuloplasty procedure, the method for steering the RVOT cerclage wire into the IVC comprises of positioning the RVOT cerclage wire in the RV through either the SVC, the CS and the inter ventricular septum, and positioning the safe-zone catheter at the PA through the IVC and the safe zone of the RV. Then a guide wire can be inserted through the safe-zone catheter which traverses through the safe zone. Once the guide wire is positioned at the PA, the safe-zone catheter is removed and the capture catheter is advanced over the guide wire through the safe zone to the PA. Once the capture catheter is positioned in the PA, the RVOT wire can be captured and steered out towards the IVC by directing the capture catheter out toward the IVC.

If the safe-zone catheter and the capture catheter is combined into one device, the method for steering the RVOT cerclage wire into the IVC comprises of first, positioning the RVOT cerclage wire at the RV after it passes through the SVC, the CS and the inter ventricular septum. Meanwhile the combined MV cerclage annuloplasty catheter is positioned at the PA after traversing through the IVC and the safe zone of the RV. Then, using the capture member of the combined MV cerclage annuloplasty catheter, the RVOT cerclage wire is captured and steered out towards the IVC by directing the combined MV cerclage annuloplasty catheter with the capture member out toward the IVC.

Once the RVOT cerclage wire is steered into the IVC, then a snare is introduced through the SVC to grab the RVOT cerclage wire from the IVC into the SVC, thus completing the circle around the MV annulus.

Figure 14:
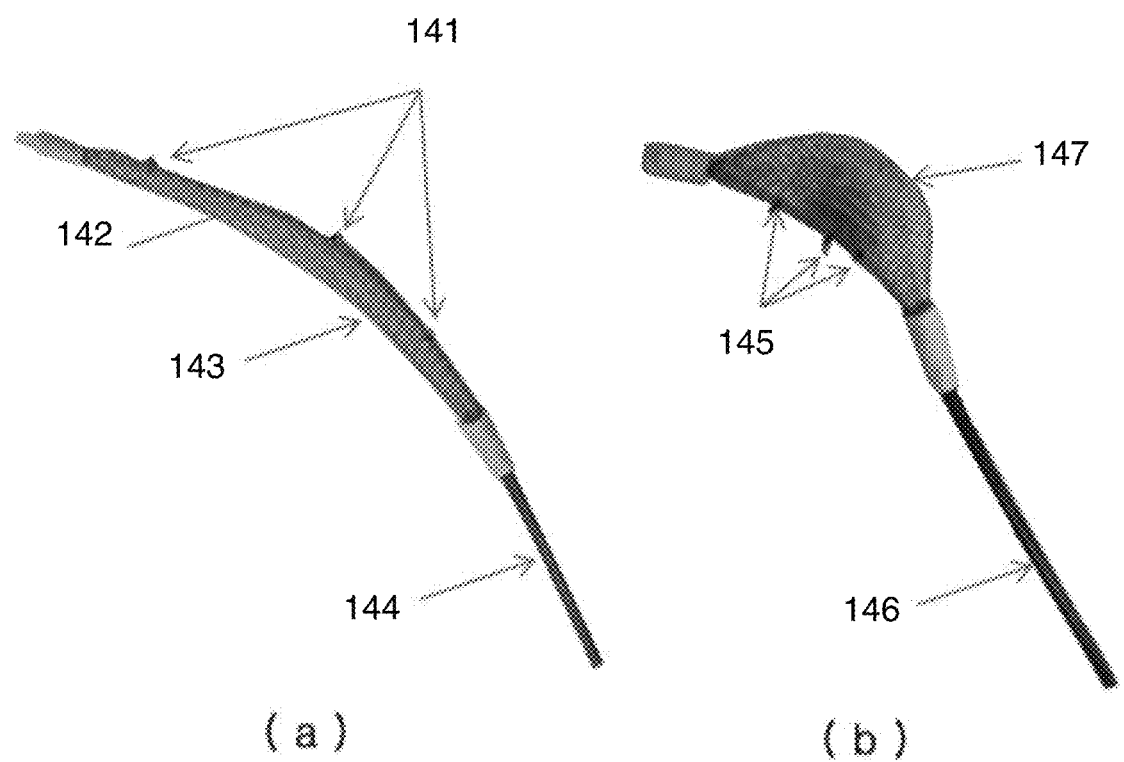
FIG. 14 shows a drawing of another embodiment of MV cerclage annuloplasty RWC device comprising a capturing catheter with a D-shaped mesh wherein FIG. 14(*a*) shows the D-shaped mesh in its collapsed state, and FIG. 14(*b*) shows the D-shaped mesh in its expanded state.
Figure 15:
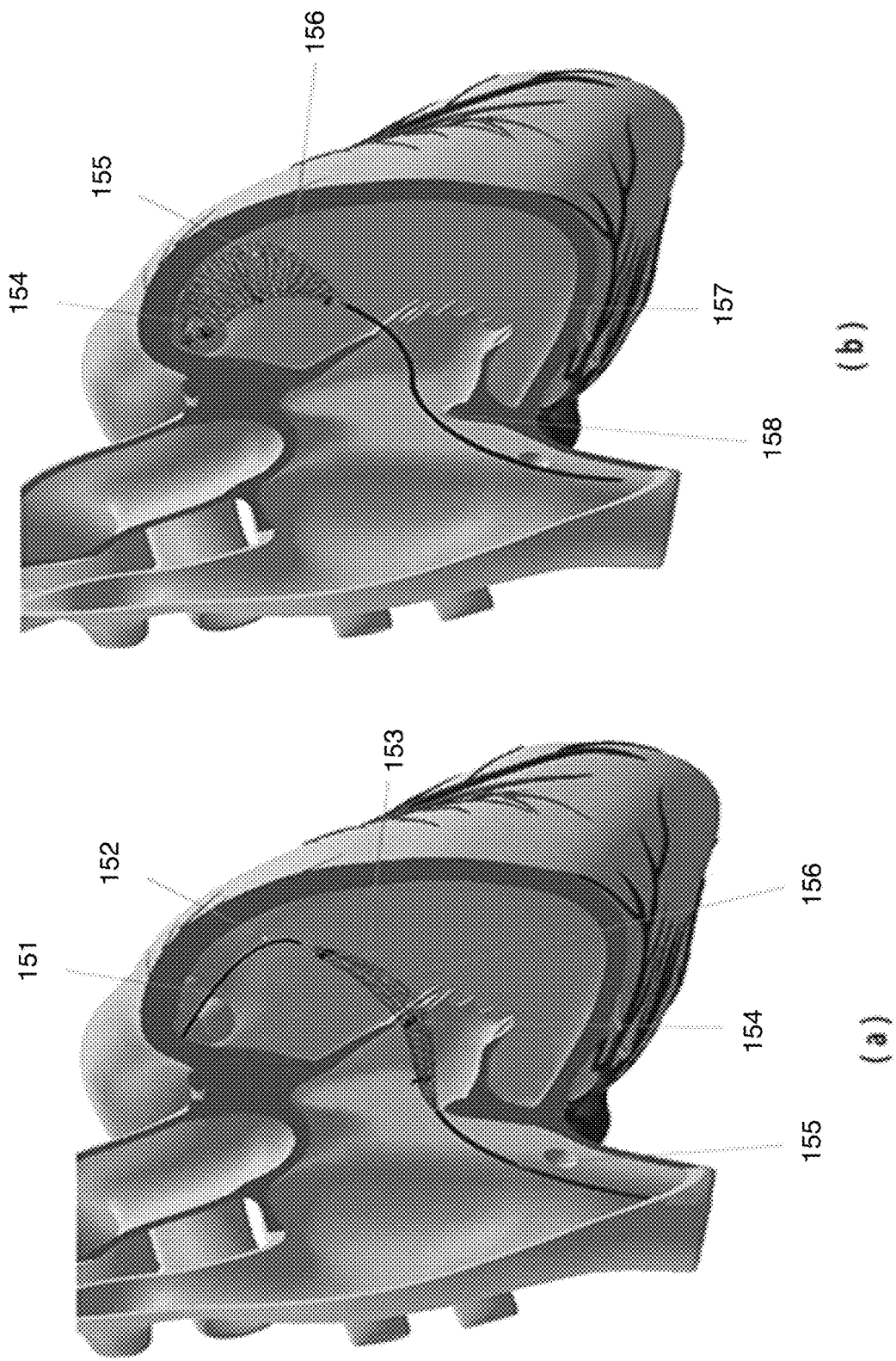
FIG. 15 shows a drawing of the capturing catheter with the D-shaped mesh in a heart, wherein FIG. 15(*a*) shows the D-shaped mesh in its collapsed state, and FIG. 15(*b*) shows the D-shaped mesh in its expanded state.

FIG. 14 shows a drawing of another embodiment of MV cerclage annuloplasty RWC device comprising a capturing catheter with a D-shaped mesh 143, 147 and FIG. 15 shows a drawing of the capturing catheter with the D-shaped mesh 155 in the heart.

FIG. 14(a) and FIG. 15(a) both show the D-shaped mesh 143 in its collapsed state, and FIG. 14(b) and the FIG. 15(b) both show the D-shaped mesh 147 in its expanded state. FIG. 15(a) shows the mesh 143 before it has completely entered the RV.

Referring to FIG. 14 and FIG. 15, the capturing catheter of the MV cerclage annuloplasty RWC device comprises of the outer catheter 122, 133, 144, 146, 155, 158, the central lumen catheter 125, 134, 142, 156, 154 and the D-shaped mesh 143, 147, 153, 156. The distal portion of the D-shaped mesh is gathered and fixed to the central lumen catheter 125, 134, 142, 156, 154 and the proximal portion of the D-shaped mesh 143, 147, 153, 156 is gathered and fixed to the outer catheter 122, 133, 144, 146, 155, 158.

The central lumen catheter 125, 134, 142, 156, 154, 410 has an open internal lumen which holds a guide wire 400, 500, 600 so that the capture catheter can be inserted over the guide wire 400, 500, 600 to the RV.

The central lumen catheter 125, 134, 142, 156, 154, 410 is placed inside lumen of the outer catheter 122, 133, 144, 146, 155, 158, 430 so that it can move back and forth within the lumen of the outer catheter.

The capture catheter is inserted over the guide wire passing through the safe zone into the RV. When the outer catheter 122, 133, 144, 146, 155, 158, 430 is pushing inwardly from the outside of the body, then the outer catheter 122, 133, 144, 146, 155, 158, 430 will move inwardly and distally over the central lumen catheter 125, 134, 142, 156, 154, 410 thus expanding the mesh 420, 510, 610, 920, 124, 135, 147.

Preferably, when the mesh is expanded, it forms the shape of the capital letter "D" conforming to the shape of the RV so that the RVOT cerclage wire which has entered the RV through the interventricular septum can more easily pass through the expanded mesh. Further, when the mesh is the shape of a capital letter "D," thus it is able to expand the most due to the anatomical shape of the RV such that the RVOT cerclage wire will naturally fall through the expanded mesh enabling precision in the ability to steer the RVOT wire into the IVC.

Referring to the FIG. 14, in the current invention, in order for the mesh 143, 147 to be in D-shape when it is expanded, the capturing catheter comprises at least one connector(s) 141, 145, 157 which attaches but does not fix the mesh to the central lumen catheter 125, 134, 142, 156, 154, 410 allowing the connector(s) 141, 145, 157 to move freely back and forth along the central lumen catheter 125, 134, 142, 156, 154, 410 so that the mesh 147 can expand and collapse forming a D-shape when the mesh is expanded. Since the connector(s) 141, 145, 157 is always attached to one side of the central lumen catheter 125, 134, 142, 156, 154, 410 when the mesh expands, it can fully expand towards the opposite, unattached side of the RV in the shape of letter "D."

Although not illustrated in the Figures, within one outer catheter, the safe-zone catheter and the capture catheter can be inserted. As discussed previously, the combined MV cerclage annuloplasty catheter with the safe-zone catheter and the capture catheter comprises of blocking member positioned proximal to the distal end of the catheter and the capture member positioned on proximal to the blocking member. Alternatively, a separate safe-zone catheter and a separate capture catheter can be positioned inside one single outer catheter.

Having illustrated and described the principles of the invention by several embodiments, it should be apparent that those embodiments can be modified in arrangement and detail without departing from the principles of the invention. Thus the invention includes all such embodiments and variations thereof, and their equivalents.

The invention claimed is:

1. A capturing apparatus for capturing a wire, the capturing apparatus comprising:
   a first catheter;
   a second catheter having a lumen configured for allowing the first catheter move therethrough the lumen; and
   a mesh having a distal end and a proximal end, the distal end of the mesh mounted on the first catheter, the proximal end of the mesh mounted on the second catheter, the mesh configured for allowing the wire to pass therethrough when the mesh is in an expanded state wherein one side of the mesh has a greater radius of curvature than the other when the mesh is in an expanded state, the mesh configured for capturing the wire when the mesh is a contracted state.

2. The capturing apparatus of claim 1 wherein the first catheter has a lumen configured for allowing a guidewire to move therethrough.

3. The capturing apparatus of claim 2, wherein the mesh is controlled by changing a position of either the first catheter, the second catheter, or both along the guidewire.

4. The capturing apparatus of claim 1, further comprising means arranged on the distal portion of the first catheter for passing blocking entrapment of the ventricular tissues.

5. The capturing apparatus of claim 1, wherein the mesh forms in a shape of a letter D.

* * * * *